(12) United States Patent
Badley et al.

(10) Patent No.: US 6,294,391 B1
(45) Date of Patent: Sep. 25, 2001

(54) SPECIFIC BINDING ASSAYS

(75) Inventors: Robert A. Badley, Bedford; Mark J. Berry, Northampton; Philip Porter, Bedford; Trevor A. Wattam, Royston, all of (GB)

(73) Assignee: Unilever Patent Holdings B.V., AT Vlaardingen (NL)

( * ) Notice: Subject to any disclaimer, the term of this patent is extended or adjusted under 35 U.S.C. 154(b) by 0 days.

(21) Appl. No.: 08/861,693

(22) Filed: May 22, 1997

(30) Foreign Application Priority Data

May 23, 1996 (EP) .................................................. 96303693

(51) Int. Cl.$^7$ .................................................. G01N 33/543
(52) U.S. Cl. ........................... 436/518; 310/311; 310/313
(58) Field of Search ................................ 310/311, 313 R, 310/340; 385/12, 129, 130; 422/55, 57, 82.05, 82.11; 435/287.1, 287.2, 288.7, 808, 972; 436/164, 512, 513, 518, 524, 525, 527, 805, 815, 819

(56) References Cited

U.S. PATENT DOCUMENTS 5,354,654 * 10/1994 Ligler et al. ............................. 435/6
5,573,956 * 11/1996 Hanning ................................. 436/518
5,641,640 * 6/1997 Hanning .............................. 435/7.92

FOREIGN PATENT DOCUMENTS

90/11525 * 10/1990 (WO) .

* cited by examiner

*Primary Examiner*—Christopher L. Chin
(74) *Attorney, Agent, or Firm*—Pillsbury Winthrop LLP

(57) ABSTRACT

Disclosed is a method of detecting the presence of an analyte of interest in a sample, the method comprising the steps of:
  providing a binding partner reversibly immobilised on a solid support, said binding partner having binding specificity for the analyte;
  contacting the sample with the solid support;
  specifically displacing the binding partner from the solid support in response to the presence of the analyte of interest in the sample, said displacement causing a reduction in the mass of material immobilised on the solid support, thereby generating a detectable change in a mass-dependent property of the solid support; and
  detecting said change. Also disclosed is an assay device for performing the method of the invention.

8 Claims, 6 Drawing Sheets

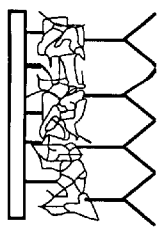
FIG. 6A
 
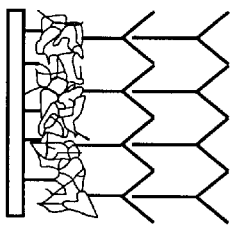
FIG. 6B
 
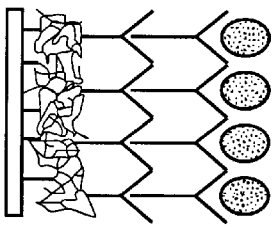
FIG. 6C
 
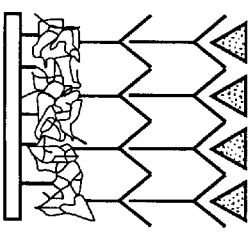
FIG. 6D
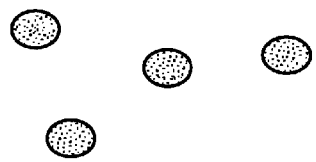

SPECIFIC BINDING ASSAYS

FIELD OF THE INVENTION

This invention relates to a method of detecting the presence of an analyte of interest, and an assay device for performing the method.

BACKGROUND OF THE INVENTION

Numerous assays have been described which make use of the specific binding properties of certain molecules to detect the presence of an analyte of interest in a sample. Typically such assays involve the specific binding between immunoglobulins (such as antibodies or functional binding fragments thereof) and haptens or antigens to which the immunoglobulins bind. Examples of such assays include enzyme-linked immunosorbent assays (ELISAs) and radio-immunoassay (RIA).

Conventionally, in order to detect binding between the analyte of interest and a binding partner having specific binding affinity therefor, it is necessary for the binding partner to be labelled. Known labels include enzymes, radio-labels, fluorescent or chemiluminescent labels, electroactive labels (such as redox labels) and coloured particles (e.g. latex beads).

A refinement of assays of the general nature outlined above relates to "displacement" assays. In such assays, the presence of an analyte of interest in a sample causes the displacement either of a labelled binding partner or a labelled ligand from a pre-existing binding partner/ligand complex. Generally speaking the amount of displaced labelled substance will be proportional to the concentration of the analyte of interest in the sample. Alternatively, one may employ "competition" assays, in which there is competition between the analyte of interest and a labelled competitor (such as labelled analyte or analogue) for binding to available binding sites.

Several assay methods relying on competition and/or displacement are described in the prior art. For example, EP 0,324,540 discloses assays designed to measure the amount of free ligand (rather than complexed ligand, which complexed ligand is typically protein-bound) in biological samples such as plasma or serum. The assay method requires the use of a "signal reagent", which is a labelled monoclonal antibody. The monoclonal binds to free ligand, which is in competition with a ligand analogue (which analogue does not bind to the natural ligand complexing proteins present in the sample). Typically the analogue is immobilised (e.g. on particles or beads). The analogue is selected to have a lower affinity than the ligand for the anti-ligand monoclonal antibody. The assay thus works on the principle of immuno-competition, the presence of free ligand in the sample serving to decrease the amount of labelled antibody which becomes associated with the ligand analogue.

WO 91/05262 discloses a device and method for detecting the presence of molecular analytes in a fluid (especially e.g. steroids, and other low molecular weight analytes). Typically, aqueous biological samples are drawn along a test strip by capillary action. As the sample advances, it carries a labelled analyte from an area of storage at one end of the strip to a first binding means, which is an anti-analyte antibody. In the absence of free analyte in the sample, the labelled analyte (e.g. analyte/enzyme conjugate) will remain bound to the first binding means. However, if free analyte is present in the sample it will tend to displace the labelled analyte (or at least, compete therewith for binding sites on the first binding means) such that some labelled analyte will be bound to the second binding means, which is an anti-enzyme antibody. Colour is developed by placing the strip in an appropriate substrate solution.

EP 0,383,313 discloses a composition and assay method "for measuring haptens, antigens or antibodies by means of a competitive binding method". The invention disclosed therein requires that either the antibody or its ligand is labelled.

However, useful as such assays are, the requirement for labelling is disadvantageous. Radio-labels represent obvious hazards in handling and disposal. Enzyme or other active labels may deteriorate during storage, affecting the sensitivity of the assay. Use of coloured particles causes problems in that the relatively large surface area of the particles introduces non-specific binding sites which can affect the accuracy of the assay.

The present invention seeks to reduce these difficulties by providing an assay method and device which do not require the use of conventionally-labelled reagents.

SUMMARY OF THE INVENTION

In a first aspect the invention provides a method of detecting the presence of an analyte of interest in a sample, the method comprising the steps of:

providing a binding partner reversibly immobilised on a solid support, said binding partner having binding specificity for the analyte;

contacting the sample with the solid support;

specifically displacing the binding partner from the solid support in response to the presence of the analyte of interest in the sample, said displacement causing a reduction in the mass of material immobilised on the solid support, thereby generating a detectable change in a mass-dependent property of the solid support; and detecting said change.

In a second aspect the invention provides a method of detecting the presence of an analyte of interest in a sample, the method comprising the steps of:

providing an analogue of the analyte of interest reversibly immobilised on a solid support;

contacting the sample with the solid support;

specifically displacing the analogue from the solid support in response to the presence of the analyte of interest in the sample, said displacement causing a reduction in the mass of material immobilised on the solid support, thereby generating a detectable change in a mass-dependent property of the solid support; and detecting said change.

Changes in the mass of material immobilised on the solid support can cause detectable changes in a number of mass-dependent properties which can be detected, for example, by acoustic wave or evanescent wave type sensors, or by surface plasmon resonance (SPR) detectors, all of which are known in the art (see, for example, those disclosed in EP 0 341 927, EP 0 416 730 and EP 0 453 224). A particularly suitable mass-dependent property for detection of changes therein is the refractive index of the surface of the solid support to which material is immobilised.

In a third aspect the invention provides a method of detecting the presence of an analyte of interest in a sample, the method comprising the steps of:

providing a binding partner reversibly immobilised on a solid support, said binding partner having binding specificity for the analyte;

contacting the sample with the solid support;

specifically displacing the binding partner from the solid support in response to the presence of the analyte of interest in the sample, said displacement generating a detectable signal; and detecting said signal;

characterised in that said binding partner does not comprise a conventional label.

In a fourth aspect the invention provides a method of detecting the presence of an analyte of interest in a sample, the method comprising the steps of:

providing an analogue of the analyte of interest reversibly immobilised on a solid support;

contacting the sample with the solid support;

displacing the analogue from the solid support in response to the presence of the analyte of interest in the sample, said displacement generating a detectable signal; and detecting said signal;

characterised in that said analogue of the analyte does not comprise a conventional label.

The invention also provides an assay device for detecting the presence of an analyte of interest in a sample, the device comprising:

a solid support; a binding partner reversibly immobilised on said solid support, said binding partner having binding specificity for the analyte of interest; and change detection means for detecting a change in a mass-dependent property of the solid support caused by specific displacement of the binding partner from the solid support in response to the presence of the analyte of interest.

The invention additionally provides an assay device for detecting the presence of an analyte of interest in a sample, the device comprising:

a solid support; an analogue of the analyte reversibly immobilised on said solid support; and change detection means for detecting a change in a mass-dependent property of the solid support caused by specific displacement of the analogue from the solid support in response to the presence of the analyte of interest.

The invention also provides an assay device for detecting the presence of an analyte of interest in a sample, the device comprising:

a solid support; a binding partner reversibly immobilised on said solid support, said binding partner having binding specificity for the analyte of interest and wherein said binding partner does not comprise a conventional label; and signal detection means for detecting a signal generated by specific displacement of the binding partner from the solid support in response to the presence of the analyte of interest.

Further, the invention provides an assay device for detecting the presence of an analyte of interest in a sample, the device comprising:

a solid support; an analogue of the analyte reversibly immobilised on said solid support, wherein said analogue does not comprise a conventional label; and signal detection means for detecting a signal generated by specific displacement of the analogue from the solid support in response to the presence of the analyte of interest.

The assay methods and devices of the invention may be used in a qualitative manner to detect the presence of the analyte of interest. They may also be used in a quantitative manner to measure the amount of analyte present.

In many embodiments the displaced binding partner or analogue of the analyte desirably do not comprise (nor are complexed with, conjugated or in any way linked to) any label whatsoever. However, in certain embodiments, as explained below, it is desirable for the displaced binding partner or analogue to comprise a non-conventional label.

The term "conventional label" as used herein refers to labels such as enzymes, radio-labels, fluorescent or chemiluminescent labels, electroactive labels (such as redox labels), and coloured particles (such as latex, or coloured or metallic sols). All of the foregoing labels are primarily detectable in some way other than by simply detecting the mass of the label substance. In the present invention, the non-conventional label relies solely on its mass to give rise to a detectable signal.

In most preferred embodiments of the present invention displacement of the binding partner or analogue of the analyte is the event which is directly detected (e.g. typically by use of an evanescent or acoustic wave type or SPR sensor) and so gives rise to a signal. It will be appreciated that in the method/device of the invention the signal is essentially generated at the site of displacement of the binding partner or analogue, rather than being "stored" in some labelled entity.

The binding partner and the analyte are conveniently members of a specific binding pair. Numerous examples of such specific binding pairs are known (e.g. DNA and DNA-binding proteins, hormones and their receptors, antigens and antibodies thereto). Typically the binding partner is a protein, preferably an immunoglobulin (e.g. antibody) or a functional binding fragment thereof, which term relates to, inter alia, Fv, scFv, Fab, $Fab_2$ and the like. In certain preferred embodiments the binding partner is a protein having specific binding activities for two distinct ligands. Examples of such proteins are bispecific antibodies or "Diabodies", which are well known to those skilled in the art.

The reversibly immobilised binding partner or analogue of the analyte may be bound to the solid support in any one of a number of ways, which will be apparent to the person skilled in the art. The binding partner or analyte analogue may normally be removed from the solid support by application of particular chemicals (e.g. solutions, such as 50 mM glycine, buffered to very low [≈pH2] or 50 mM diethylamine buffered to very high pH [≈pH 12] and the like) but, under conditions in which the assay is performed (such as those generally found in biological systems), will be released from the solid support only by the presence of the analyte of interest. Typically the sample assayed will be a biological sample (such as a body fluid e.g. urine, whole blood or serum), and the assay conditions will be broadly physiological (e.g. about 10–40° C., about pH 5–9), such that the binding partner or analyte analogue will only be released from the solid support by the presence of the analyte of interest.

The assay method of the invention may be performed, or the assay device used, in any one of several different formats. For example, the reversibly immobilised binding partner may be an immunoglobulin, bound to a solid support via interaction with an antigen, which is the analyte of interest. The presence in the sample of high concentrations of the free antigen will tend to cause displacement of the immunoglobulin from the solid support. Such an assay will generally be effective only when there is a high concentration of free analyte of interest in the sample.

Conveniently, in one embodiment, an analogue of the analyte of interest is immobilised (preferably via covalent interactions) on a solid support. Methods suitable for accomplishing this are well known to those skilled in the art. A binding partner specific for the analyte is then allowed to bind (comparatively loosely) to the analogue of the analyte (e.g. via non-covalent interactions), so as to reversibly immobilise the binding partner to the solid support. A preferred embodiment of the invention therefore has an immunoglobulin bound to a solid support via a non-covalent interaction with an analogue of the analyte of interest (the analogue typically being covalently bound to the solid support), the immunoglobulin having a lower affinity for the analogue than for the analyte. Accordingly, the presence of the analyte of interest in the sample, even at low concentrations, will tend to cause displacement of the immunoglobulin. Desirably, the binding affinity of the immunoglobulin for the analyte of interest is between 5 and 100 times greater than its affinity for the analogue, typically between 10 and 20 times greater.

For reasons which will become apparent, the method/device of the invention finds particular advantage when applied to the detection of relatively low molecular weight analytes (e.g. steroids and the like) having molecular weights of around 5 kD or less. One such analyte is the steroid estradiol, or metabolites thereof such as estrone-3-glucuronide. Thus, for example, where the analyte of interest is estrone-3-glucuronide, a suitable analogue thereof for use in detecting the presence of the analyte in accordance with the invention may be estriol-3-glucuronide. Other possibly suitable analogues will be apparent to those skilled in the art and include, for example, estrone, estrone-3-sulphate, estriol, estradiol and estradiol-3-glucuronide. In general, the analogue will typically be a compound which shares a degree of structural similarity with the analyte, such that certain biological molecules (e.g. antibodies, receptors) which bind to the analyte will also bind to the analogue, albeit with lower binding affinity. Where the analyte is a peptide or polypeptide, the analogue will conveniently comprise one or more amino acid residue substitutions relative to the analyte.

In an alternative embodiment, the assay method of the invention may involve displacement not of a binding partner of the analyte, but of an analogue of the analyte. For example, an immunoglobulin may be immobilised on a solid support in such a way that at least one antigen binding site is available for binding antigen. Typically, prior to performance of the assay, substantially all of the available binding sites are occupied by an analogue of the analyte of interest, the immunoglublin having a lower binding affinity for the analogue than for the analyte of interest such that, upon addition of a sample containing the analyte of interest, the analogue will be displaced from the binding site of the immunoglobulin.

The immunoglobulin (e.g. IgM) could have a plurality of binding sites such that one binding site interacts with antigen bound to a solid support, leaving another free to be occupied by analyte analogue prior to assay. Alternatively, the antibody could possess a single binding site (like Fv or Fab fragments of Ig) but be immobilised to a solid support in such a way that the single binding site is available for occupation. Immunoglobulin molecules (such as IgG) may conveniently be immobilised via an anti-Fc antibody, as described in Example 2 below.

Thus, in one embodiment, an anti-Fc antibody is immobilised (typically via a covalent interaction) upon a solid support. A second antibody, specific for the analyte of interest, is then captured on the solid support by the anti-Fc antibody. The binding sites of the analyte-specific antibody are then substantially fully occupied by an analogue of the analyte of interest, such that the analogue is reversibly immobilised upon the solid support via non-covalent interaction with the analyte-specific antibody. The affinity of the analyte-specific antibody for the analyte of interest is desirably between 5 and 100 times greater than its affinity for the analogue.

Conveniently, the solid support comprises part of a biosensor device. A biosensor may be defined as an analytical device which comprises a biological molecular recognition component, which device typically produces an electronic signal dependent on the presence and/or concentration of an analyte interacting with the biological recognition component. Such biosensor devices are well-known and are described, for example, in EP 0 341 927, EP 0 416 730 and EP 0 453 224. Preferably the biosensor detects a change in a mass-dependent property of the solid support (e.g. speed of propagation of an acoustic wave, propagation of an evanescent wave, or SPR). Examples of such devices which utilise the evanescent wave or SPR phenomena (Hutchinson 1995 Molecular Biotechnology 3, 47–54 and references therein) include the BIAlite™ and BIAcore™ devices sold by Biacore AB, the IAsys™ device sold by Affinity Sensors Limited (UK), and the BIOS-1 device sold by Artificial Sensor Instruments (Zurich, Switzerland).

Displacement of antibody molecules from the sensor surfaces of such devices causes a relatively large decrease in mass, which is readily detectable. However, in those embodiments where an analogue of the analyte of interest is displaced by the analyte, it will be apparent to those skilled in the art that, for evanescent wave-type sensors and other mass-dependent biosensors, the analogue must have a sufficiently higher molecular weight than the analyte, otherwise the net change in mass may be very small and thus difficult to detect.

For example, where the analyte is a low molecular weight compound, such as a steroid or a peptide, the analogue may be conjugated to a high molecular weight substance so as to create a higher molecular weight difference between the analyte and the analogue. High molecular weight substances suitable for conjugation include proteins such as ovalbumin or bovine serum albumin (BSA), or other entities such as lipids and the like. It is to be noted that these substances are not conventional labels such as enzymes, radiolabels, fluorescent or chemiluminescent tags, redox labels or coloured particles and the like, but serve merely to create a disparity in molecular weight between the analyte and the analogue.

Alternatively, where the analyte is a peptide, the molecular weight of the analogue may be increased relative to the analyte, by using the peptide as part of a fusion protein. Conveniently the peptide may be fused to the N-terminal or, more preferably, the C-terminal of a polypeptide. Methods for the construction of DNA sequences encoding such fusion proteins are well known to those skilled in the art.

The added molecular mass represented by the polypeptide may be viewed as a non-conventional label. However, the fused or, as may be the case conjugated, polypeptide need not retain any particular activity unlike, say, an enzyme label, so that the assay component will not become less sensitive due to loss of activity during storage. Similarly, the use of a single polypeptide rather than a comparatively large latex bead (as in the prior art) will introduce comparatively few non-specific binding sites, such that the accuracy of the assay will not be adversely affected.

BRIEF DESCRIPTION OF THE FIGURES

FIGA. 1A and 1B shows the structural formulae of the compounds FIG. 1A (I) estrone β-D-glucuronide (abbreviated as estrone-3-glucuronide or E3G) and FIG. 1B (II) estriol 3-(β-D-glucuronide) (abbreviated as estriol-3-glucuronide), which compounds are utilised in Example 1 below;

FIGS. 6A–6D are a schematic representation of the assay format described in Example 2 below;

DETAILED DESCRIPTION OF THE INVENTION

Example 1

In this example an assay is described which utilises surface plasmon resonance (SPR). This phenomenon has now been described in several publications and is the basis of evanescent wave biosensors (for a review, see Hutchinson 1995 cited above).

In summary, light incident on an interface between two media of different refractive indices will, at a specific angle of incidence, generate a resonant "evanescent" wave. The resonance is extremely sensitive to changes in the refractive index of the media. A change in the refractive index causes resonance to occur at a new angle of incidence. The change in refractive index is caused by mass binding to a thin gold film at the interface between the two media: the change in refractive index is proportional to the mass bound to the gold film.

Figure 1A:
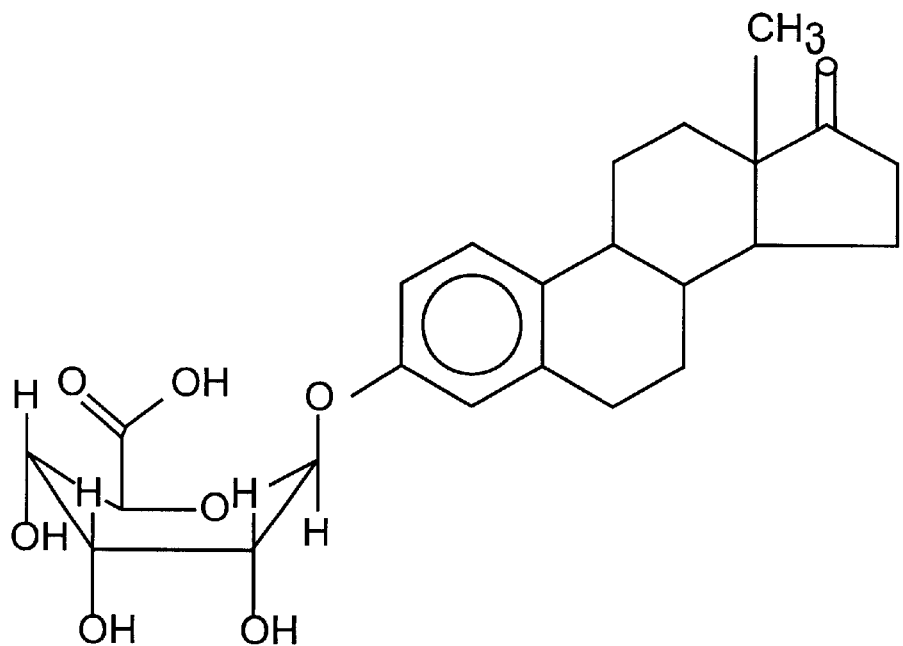
Figure 1B:
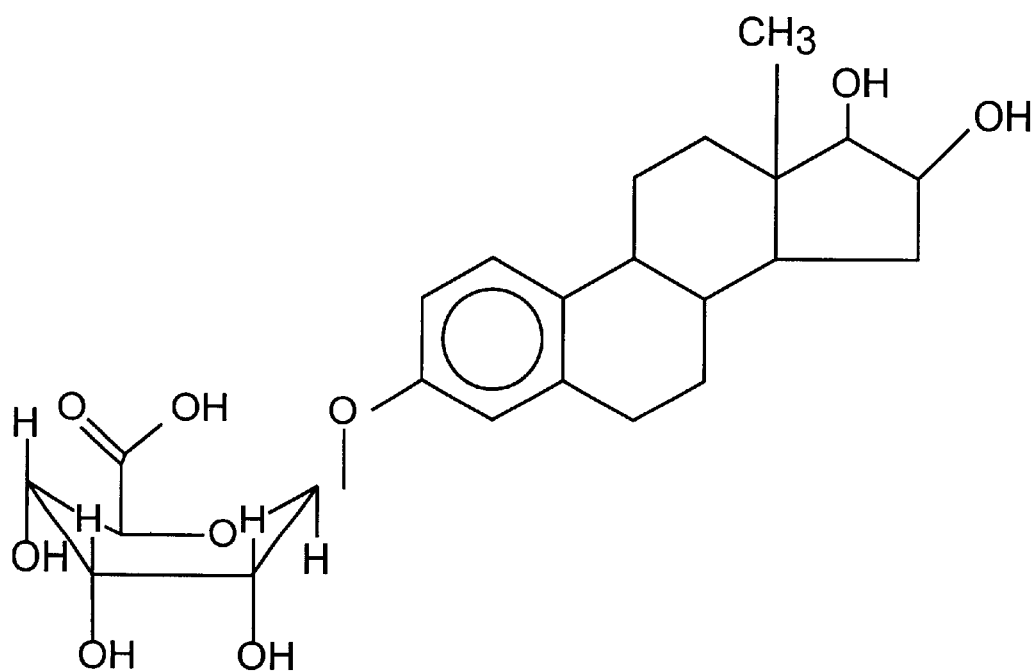

This example concerns an assay for the detection of estrone-3-glucuronide (a steroid hormone metabolite) and involves use of an analogue thereof, estriol-3-glucuronide. Details of the structures of these compounds are shown in FIGS. 1A and B.

Further by way of information this example makes use of the Pharmacia BIAlite™ evanescent wave biosensor (Jonsson et al., 1991 BioTechniques II, 620–627).

Figure 2A:
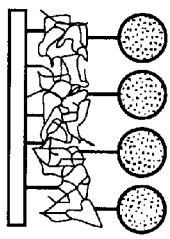
FIGS. 2A–2C is a schematic representation of the assay format described in Example 1 below.
Figure 2B:
Figure 2B:
Figure 2B:
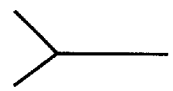
Figure 2B:
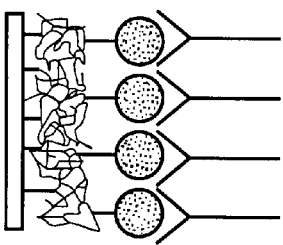
Figure 2C:
Figure 2C:
Figure 2C:
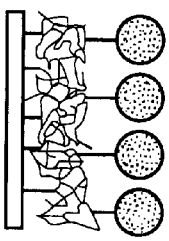
Figure 2C:
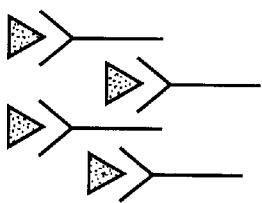

FIGS. 2A–C schematically illustrates the assay method. In step "A", an analogue (estriol-3-glucuronide, denoted in FIG. 2 by a solid circle) of the analyte of interest (estrone-3-glucuronide denoted by a solid triangle) was covalently immobilised on the activated dextran-coated surface of a solid support (a sensor chip of the Pharmacia BIAlite™ biosensor). In step "B", antibody (monoclonal 4155, denoted by the Y shape) specific for estrone-3-glucuronide was then allowed to bind to the immobilised analogue. The antibody has comparatively low binding affinity for the analogue, such that the antibody is relatively loosely held (reversibly immobilised) on the biosensor chip. Introduction of a sample containing the analyte of interest (for which the antibody has comparatively high binding affinity) will therefore cause the antibody to bind preferentially to the analyte (step "C") rather than to the immobilised analogue, so causing displacement of the antibody from the sensor chip, which displacement can be readily detected by the sensor device.

As a first step, estriol-3-glucuronide was immobilised on a sensor chip in the BIAlite™ biosensor. The method of immobilisation was essentially as described by Johnsson et al. (1995 J. Molec. Recognition 8, 125–131) and by O'Shanessy et al. (1992 Analytical Biochemistry 205, 132–136). In summary, the process was as follows:

A CM5 sensor chip was docked in to the Bialite™ instrument and equilibrated in the HBS running buffer. The instrument pump flow rate was set to 5 μl/min and temperature was maintained at 25° C.

The dextran surface was then activated using the 1-ethyl (dimethylaminopropyl)carbodiimide (EDC) and N-hydroxysuccinimide (NHS) activating chemicals from the Pharmacia amine coupling kit by injecting the EDC/NHS mixture into the sample loop and loading 35 μl over the dextran surface. EDC/NHS activation can be seen at position (1) on the sensorgram in FIG. 3.

After the surface was activated by EDC/NHS 20% (v/v), ethylene diamine (EDA) (Fluka, Code 03550) in water was injected into the sample loop. 35 μl of this solution was loaded over the surface. This changes the surface groups from carboxyl to amine derivatised. This can be seen at position (2) on the sensorgram in FIG. 3.

Estriol-3-glucuronide (Sigma, Code E-2002) was dissolved at 1.1 mg/ml concentration in EDC/NHS activation mixture and left to react for 7 minutes. This solution was then injected into the sample loop and 57 μl of this solution was loaded over the dextran/EDA surface. This can be seen at position (3) on the sensorgram in FIG. 3.

The sensor chip was then washed with HEPES-buffered saline (HBS).

The assay was performed as follows:

i) The estriol-3-glucuronide sensor chip was docked in the BIAlite™ instrument and equilibrated with HBS running buffer. The temperature was maintained at 25° C. and pump flow rate kept at 5 μl/min.

ii) Mouse monoclonal antibody specific for estrone-3-glucuronide (produced by cell line "4155") was diluted to 30 μg/ml in HBS buffer. This solution was injected into the sample loop and 35 μl was loaded over the biosensor chip surface. The 4155 monoclonal cell line was prepared and screened according to the methods described by Gani et al., (1994 J. Steroid Biochem. Molec. Biol. 48, 277–282). The Gani et al. publication relates to development of anti-progesterone antibodies, but essentially identical techniques were employed in producing antibodies reacting with estrone and analogues thereof. Antibodies other than that obtainable from cell line 4155 may readily be produced by those skilled in the art (using such techniques): such antibodies would have qualitatively similar properties. Moreover, a commercially available anti-estrone glucuronide monoclonal antibody (from Wallaceville Animal Research Centre, New Zealand) is described in Linscott's Directory of Immunological and Biological Reagents (9th edition, 1996–7).

iii) Estrone-3-glucuronide (Sigma product code E1752) was dissolved in HBS buffer at 1 mg/ml. This was diluted further to 20.5 nM, 2.05 nM and 0.205 nM concentrations with HBS buffer respectively. The concentrations used represent the physiological concentrations of E3G found in urine (Stancyzk et al., 1930 Am. J. Obs. & Gynae. 137(4), 443–450). The 20.5 nM E3G solution was injected into the sample loop and 35 µl was loaded over the biosensor chip surface to displace the bound 4155 antibody.

iv) After the injection was complete the remaining antibody was removed using a 10 µl loading of 100 mM HCl over the biosensor chip surface.

v) Steps (ii) to (iv) were repeated using the estrone-3-glucuronide dilutions at 2.05 nM and 0.205 nM respectively.

Preparation of sensor chip

Figure 3:
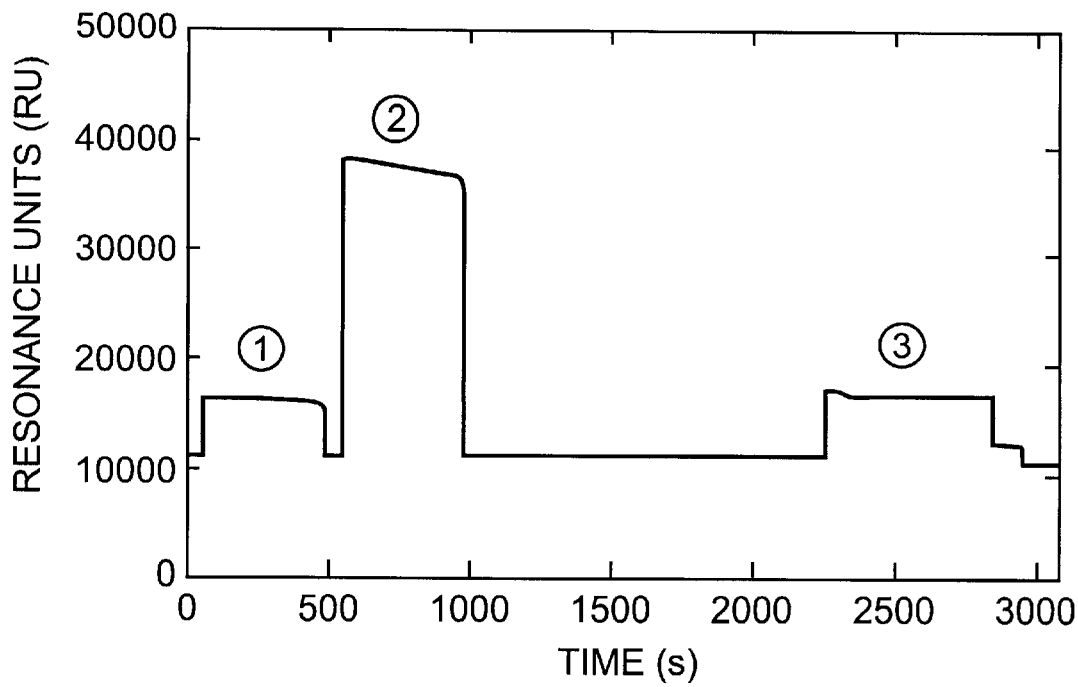
FIG. 3 is a sensorgram (arbitary Resonance Units, "RUs", against time measured in seconds) showing the preparation of an estriol-3-glucuronide sensor chip.

The sensorgram for the immobilisation of the sensor chip is shown in FIG. 3. The steroid coupled to the surface cannot be detected by looking at the sensorgram trace and comparing the baseline before immobilisation and after immobilisation. This is because the estriol-3-glucuronide molecular weight is below the limit of detection for the BIAlite™.

Figure 4:
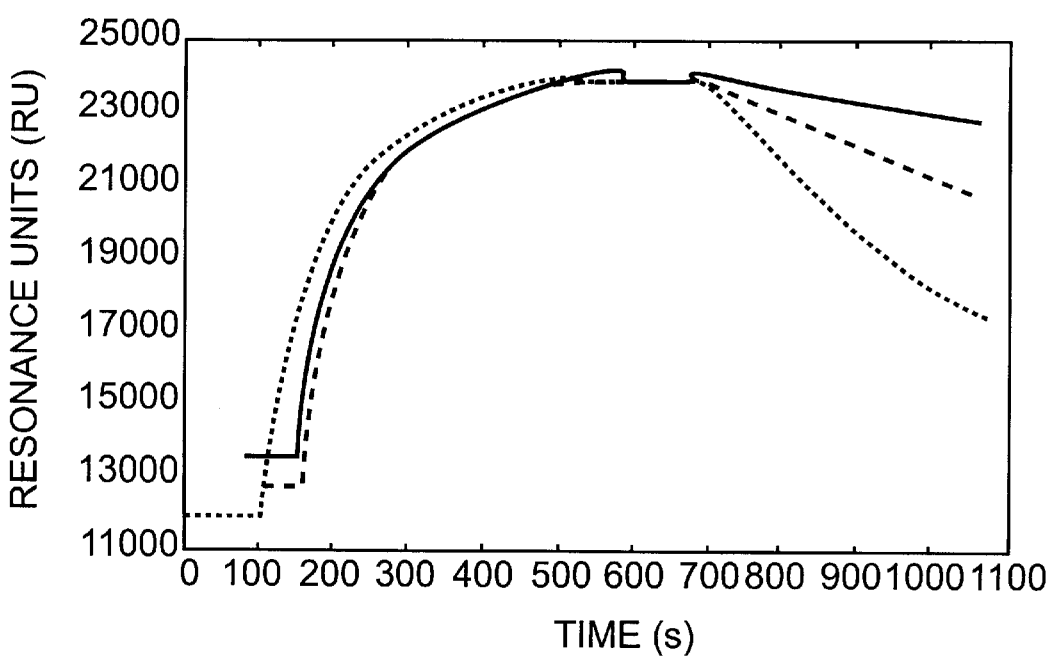
FIG. 4 is a graph of Resonance Units against time (seconds), showing displacement of 4155 antibody by estrone-3-glucuronide.
Figure 5:
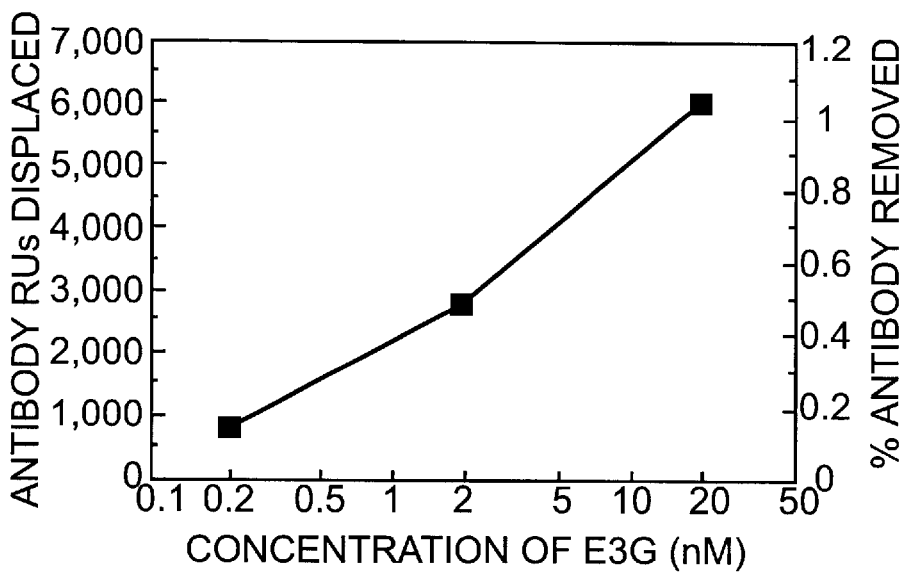
FIG. 5 is a graph of amount of 4155 antibody displaced (RUs) against concentration of estrone-3-glucuronide (nM)

Investigation of the displacement reaction with the estriol-3-glucuronide sensor chip The 4155 antibody was able to bind in large amounts to the estriol-3-glucuronide that had been covalently linked to the sensor chip. The 4155 antibody was displaced from the surface of the chip upon injection of the estrone-3-glucuronide. The amount of antibody displaced by the estrone-3-glucuronide was dependant on the steroid concentration (see FIG. 4: the solid line shows results using 0.2 nM E3G, the dashed line shows results obtained with 2.0 nM E3G, the dashed line shows results obtained with 2.0 nM E3G, and the dotted line shows results obtained with 2.0 nM E3G, and the dotted line shows results obtained using 20 nM E3G). To show this was a linear correlation a graph (FIG. 5) was drawn plotting steroid concentration against (i) the amount of antibody displaced in RUs (left hand vertical axis) and (ii) the % of antibody displaced compared to the amount bound to the surface (right hand vertical axis).

The concentrations of estrone-3-glucuronide (E3G) used in the experiment span the physiological range of E3G concentrations found in human urine samples. In the displacement experiment, it is clearly seen that the amount of antibody displaced by the E3G steroid is directly proportional to the concentration of the E3G (see FIG. 5).

This displacement reaction demonstrates the possibility of measuring small molecular ligands with the biosensor that themselves are below the minimum threshold for detection by surface plasmon resonance with the BIAlite™ instrument. The displacement reaction can form the basis of new immunoassay formats that requires no labelling of reagents with enzymes or radioactive molecules. All that is required for this type of assay to work is a low affinity antigen analogue that can be immobilised to the dextran.

Example 2

Displacement of crossreactive synthetic peptide ovalbumin conjugates from HMFG1 antibody A schematic illustration of this displacement reaction can be seen in FIGS. 6A–D.

Referring to FIGS. 6A–D, the solid support is the sensor chip of the Pharmacia BIAlite™ biosensor, coated with activated dextran. A first antibody (polyclonal rabbit anti-mouse immunoglobulin G ["RAM"] specific for the Fc portion of IgG), was covalently immobilised to the activated dextran ("A"). Next, a second (mouse) antibody, specific for the analyte of interest, is added ("B"). The analyte of interest in this example is a peptide (KPDQR) derived from human milk fat globulin (HMFG)1 protein. The anti-HMFG1 monoclonal antibody is described by Taylor-Papadimitriou et al (1981 Int. J. Cancer 28, 17). The anti-HMFG1 monoclonal antibody is captured on the sensor chip by the RAM first antibody. The first and second antibody molecules are shown in Figure by the Y shapes.

Next an analogue (peptide CPDTR using the single letter amino acid code) of the peptide analyte of interest was introduced. In this example, both the analyte and the analogue are low molecular weight peptides, which cannot readily be distinguished by differences in molecular weight. Accordingly, a high molecular weight polypeptide (ovalbumin) was chemically conjugated to the peptide analogue. This peptide-ovalbumin conjugate (shown in FIG. 6 as a solid oval shape) was bound with relatively low affinity by the anti-HMFG1 antibody, such that the analogue was reversibly immobilised on the solid support (C). When the peptide analyte of interest (KPDQR, shown in FIG. 6 as a solid triangle) was introduced, the anti-HMFG1 tended to bind preferentially thereto (having a higher affinity for the analyte of interest than for the analogue). Accordingly ("D") the analyte became bound to the sensor chip and the higher molecular weight analogue-ovalbumin conjugate was displaced. The change in mass bound to the sensor chip can be detected by the BIAlite™ device.

a) Preparation of polyclonal rabbit anti-mouse immunoglobulin G (Fc specific) sensor chip i) A carboxy methyl dextran (CM5) sensor chip (Pharmacia, Code BR-1000-14) was docked in to the BIAlite™ instrument and equilibrated in the HEPES buffered saline (HBS) (Pharmacia, Code BR-1001-88). The instrument pump flow rate was set to 5 µl/min and temperature was maintained at 25° C.

ii) The dextran surface was then activated using the EDC and NHS activating chemicals from the amine coupling kit (Pharmacia, Code BR-1000-50). EDC/NHS mixture was injected into the sample loop and 35 µl of this solution loaded over the dextran surface. EDC/NHS activation can be seen at position (1) on the sensorgram in FIG. 7.

iii) Polyclonal rabbit anti-mouse immunoglobulin G (Fc specific) (RAM Fc) (Pharmacia. code BR-1000-57) was diluted down to 50 µg/ml in 10 mM acetate buffer pH5.0 and injected into the sample loop. 35 µl of this solution was loaded over the dextran surface. The coupling of the RAM Fc to the dextran can be seen at position (2) on the sensorgram in FIG. 7.

iv) Once the RAM Fc loading was complete and unbound RAM Fc washed from the dextran surface by HBS running buffer, the remaining activated ester sites on the dextran surface were reacted with ethanolamine. 1M ethanolamine pH8.5 (Pharmacia amine coupling kit, Code BR-1000-50) was injected in to the sample loop and 35 µl loaded over the dextran/RAM Fc surface. This can be seen at position (3) on the sensorgram in FIG. 7.

v) To remove any non-covalently attached RAM Fc from the surface 100 mM HCl was injected in to the sample loop and 10 µl of this solution was loaded over the dextran/RAM Fc surface. This can be seen at position (4) on the sensorgram in FIG. 7.

b) Preparation of synthetic peptides Cys-Pro-Asp-Thr-Arg (CPDTR) and Lys-Pro-Asp-Gln-Arg (KPDQR) for the displacement reaction The peptides used here were modified variants of the natural epitope Pro-Asp-Thr-Arg (PDTR) sequence in the human milk fat globulin 1 protein to which the antibody anti-HMFG1 binds (Briggs et al., 1991 Immunology 73, 505–507). The Cys (C) in CPDTR was added to allow the peptide to be coupled to commercially available maleimide activated ovalbumin and create a useful conjugate. This conjugate is required since the peptide alone does not have sufficient mass to be detected by the BIAlite™ instrument. There is a threshold of about 5000 daltons of mass required before molecules will register with the BLAlite™ instrument.

Whilst the work described in this example relates to experiments performed with the monoclonal antibody HMFG1, other antibodies having qualitatively similar properties may readily be produced by those skilled in the art. Moreover, a commercially available anti-milk fat globulin monoclonal antibody (from Paesel & Lorei GmbH, Hanau, Germany) is described in Linscott's Directory of Immunological and Biological Reagents (9th edition, 1996–7).

In the work done to identify the critical aminoacid residues within the HMFG1 epitope (Price et al., 1991 J. Immunological Methods 139, 83–90) a number of variants were created that had affinities differing from the native PDTR sequence. Pro-Asp-Gln-Arg (PDQR) is an analogue of the PDTR sequence that has a higher affinity for the HMFG1 antibody than PDTR. The peptide KPDQR was synthesised with an N-terminal lysine to improve the solubility of the peptide. However, as this peptide contained the PDQR sequence it was also suitable for investigating the immunodisplacement reaction. The N-terminal lysine could be readily omitted without substantial deleterious effect.

i) Peptides were synthesised on a Novabiochem GEM semi-automatic synthesizer, using standard techniques as previously published (Merrifield, 1963 J. Am. Chem. Soc. 85, 2149–2154). Briefly, Fmoc-aminoacid reagents (Novabiochem) were activated sequentially using PyBOP chemistry (Grant, 1992 "Synthetic peptides. A user's guide" pub. W H Freeman & Co New York). These activated aminoacids were coupled to the solid support Novasyn TGR resin (0.8 g) (Novabiochem) to produce the protected peptide attached to a solid matrix. Dimethylformamide (DMF) solvent was used throughout the synthesis. The peptides were reacted with acetic anhydride (10% in DMF) to block the N-termini.

ii) The peptide was then deprotected and cleaved using standard cleavage conditions with 20 ml of cleavage solution per peptide [92.5% (v/v) Trifluoroacetic acid (TFA) (Aldrich), 2.5% (v/v) Ethanedithiol (Aldrich), 2.5% (v/v) water, 2.5% (v/v) triisopropylsilane (Aldrich)]. The solution was filtered to remove the resin and rotary evaporated under vacuum at 30° C. with cold finger (dry ice/acetone) trap to remove all excess solvents. This procedure took 30 minutes.

iii) Residual chemical contaminants were removed by precipitating the peptide with diethyl ether (Aldrich) and repeated extraction of this precipitate with excess diethyl ether.

iv) The peptide precipitate was then solubilised with water and freeze dried. The resulting powder was stored at −20° C. until required.

c) Preparation of the CPDTR peptide ovalbumin conjugate

Peptide was dissolved in phosphate buffered saline (PBS) to a concentration of 5 mg/ml and mixed with 5 milligrams of preactivated maleimide ovalbumin (Pierce) dissolved in 1 ml of PBS. This mixture was left to react at room temperature for 2.5 hours. The excess peptide was then removed by dialysing the sample against 5L of PBS+0.1% sodium azide (Sigma,) for 16 hours at 4° C.

The conjugate was then removed from dialysis and stored at 4° C. until required.

d) Displacement of the CPDTR peptide-ovalbumin conjugate from monoclonal HMFG1 antibody with KPDQR peptide The polyclonal rabbit anti-mouse antibody (Fc specific) biosensor chip was placed into the BLAlite™ instrument and the docking procedure executed. The HEPES buffered saline (HBS) running buffer (Pharmacia product code BR-1001-88) flow rate was then set at 5 $\mu$l/min.

Figure 7:
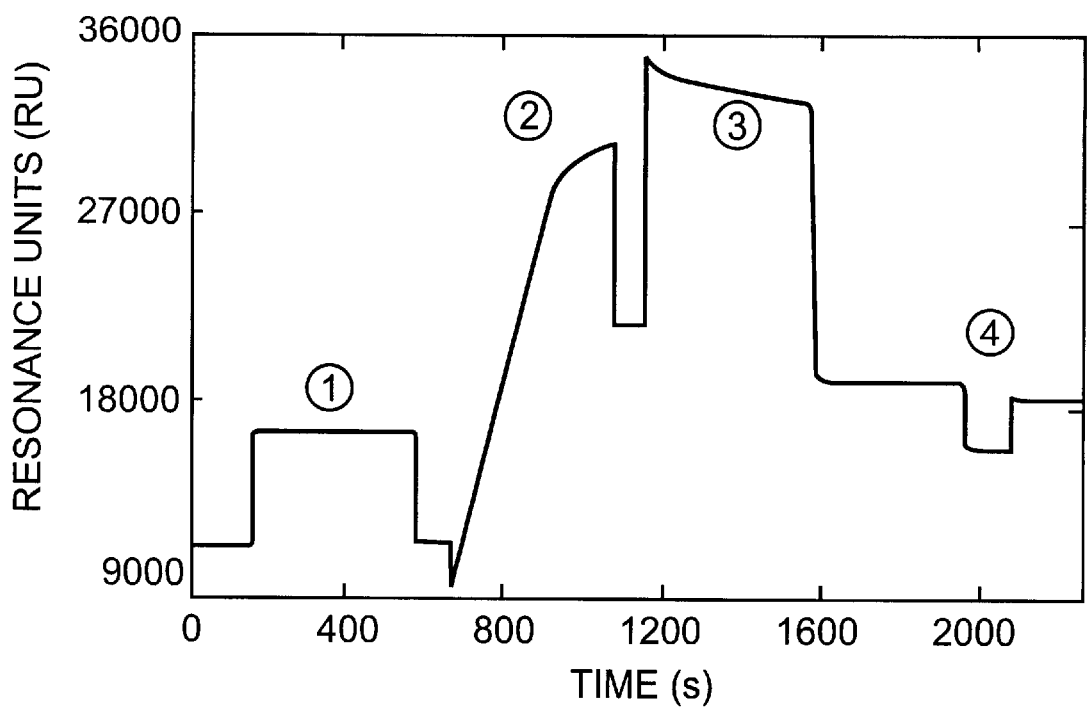
FIG. 7 is a sensorgram (arbitary Resonance Units against time, in seconds) showing the preparation of a Rabbit anti-mouse (RAM) Fc sensor chip.

A typical sensorgram for the preparation of the RAM Fc sensor chip is shown in FIG. 7. Referring to FIG. 7, 1 represents the EDC/NHS activation of the dextran surface, 2 represents the RAM Fc coupling to the activated dextran, 3 represents blocking of residual activated dextran sites with ethanolamine, and 4 represents a 100 mM HCl pulse to remove non-covalently bound substances.

Mouse monoclonal antibody specific for human milk fat globulin 1 was diluted to 50 $\mu$g/ml in HBS buffer and 35 $\mu$l of this solution was injected in to the biosensor chip. After injection the biosensor chip was automatically washed and 1040 RU of the mouse HMFG1 specific antibody had been bound by the polyclonal rabbit anti-mouse antibody (Fc specific) antibody.

The CPDTR-ovalbumin conjugate was diluted tenfold with HBS buffer and 35 $\mu$l of this solution was injected into the biosensor chip. Approximately 204 resonance units were bound by the mouse HMFG1 specific antibody. Peptide KPDQR was dissolved to 200 $\mu$g/ml in HBS buffer and 35 $\mu$l of this solution was injected into the biosensor chip to displace the CPDTR-ovalbumin conjugate.

The residual bound CPDTR-peptide conjugate and mouse anti-HMFG1 were then removed by washing the sensor chip briefly with 100 mM HCl.

A control experiment was performed in an identical manner except no peptide Lys-Pro-Asp-Gln-Arg was injected.

Results

Preparation of RAM Fc sensor chip

The coupling of the sensor chip resulted in a high capacity RAM Fc specific sensor chip that had approx 8000 RU of RAM Fc immobilised at the end of the procedure (see FIG. 7). The RAM Fc binds the mouse HMFG1 antibody with multiple binding sites for each antibody molecule, thus giving a high avidity for the molecule. The effect of the high avidity is negligible dissociation of the monoclonal antibody from the RAM Fc layer. This can be seen at position 2 in FIG. 8 where there is almost a flat line for the dissociation of HMFG1 from RAM Fc. This condition is required in order to ensure that any loss of RUs in the displacement experiment is due to immunospecific displacement of CPDTR-ovalbumin by the KPDQR peptide, and not the HMFG1 monoclonal antibody dissociating from the RAM Fc layer.

Figure 8:
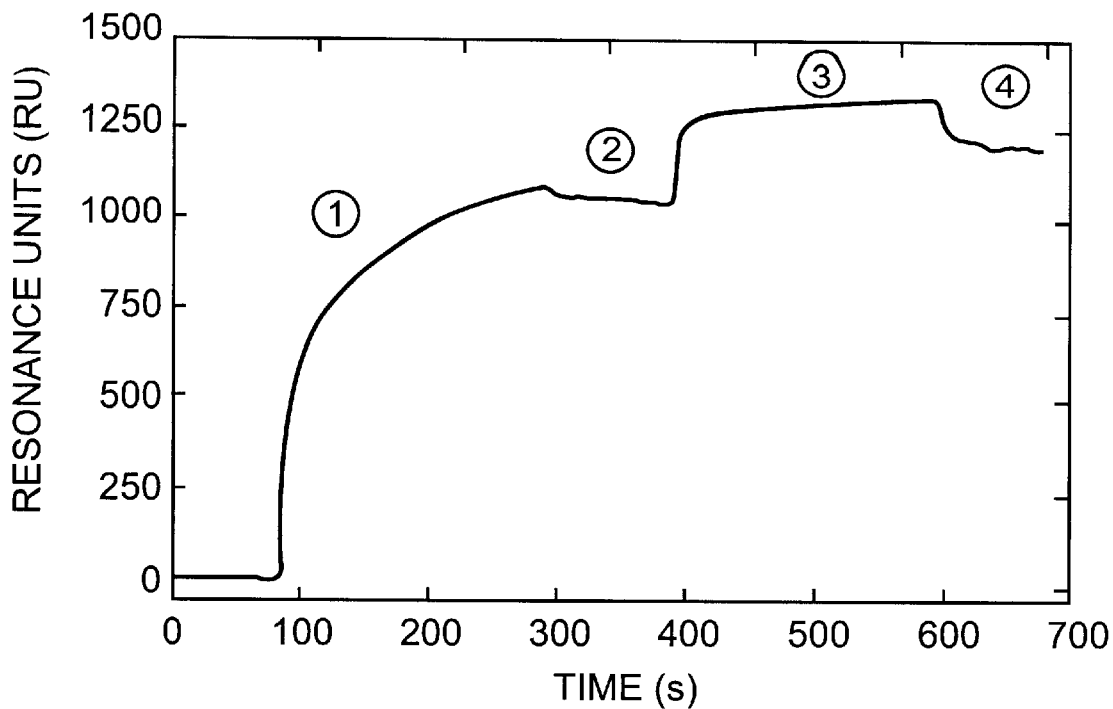
FIG. 8 is a sensorgram (Resonance Units against time, in seconds) showing binding of anti-human milk fat globulin HMFG1 antibody to a RAM Fc sensor chip, and binding of CPDTR peptide-conjugate to the HMFG1 antibody.

In FIG. 8, (1) represents HMFG1 binding to the RAM Fc sensor chip, (2) represents dissociation of HMFG1 antibody from RAM Fc layer, (3) represents CPDTR-ovalbumin conjugate binding to HMFG1 antibody, and (4) represents dissociation of CPDTR-ovalbumin conjugate from HMFG1 antibody.

The SPR signal from molecular binding events is reduced by the mass of the molecule and the distance the event occurs from the resonating gold layer. Molecular interaction studies that require several layers of molecules to be assembled have to compensate for the reductions in signals that occur as each layer of molecules is added and the distance from the gold layer increased. Compensating for this problem is achieved by immobilising large amounts of ligand in the first layer of the test system. This overcomes the signal reductions and the final molecular binding events are easily observed.

The RAM Fc sensor chip was capable of binding 1000 RU of mouse monoclonal HMFG1 antibody. This was sufficient to ensure that binding of the CPDTR-ovalbumin peptide conjugate to HMFG1 antibody and any displacement effect by peptide KPDQR on the CPDTR-ovalbumin conjugate bound to HMFG1 antibody would be easily observed (see FIG. 8).

Displacement of CPDTR-ovalbumin conjugate from HMFG1 antibody by peptide KPDQR

Figure 9:
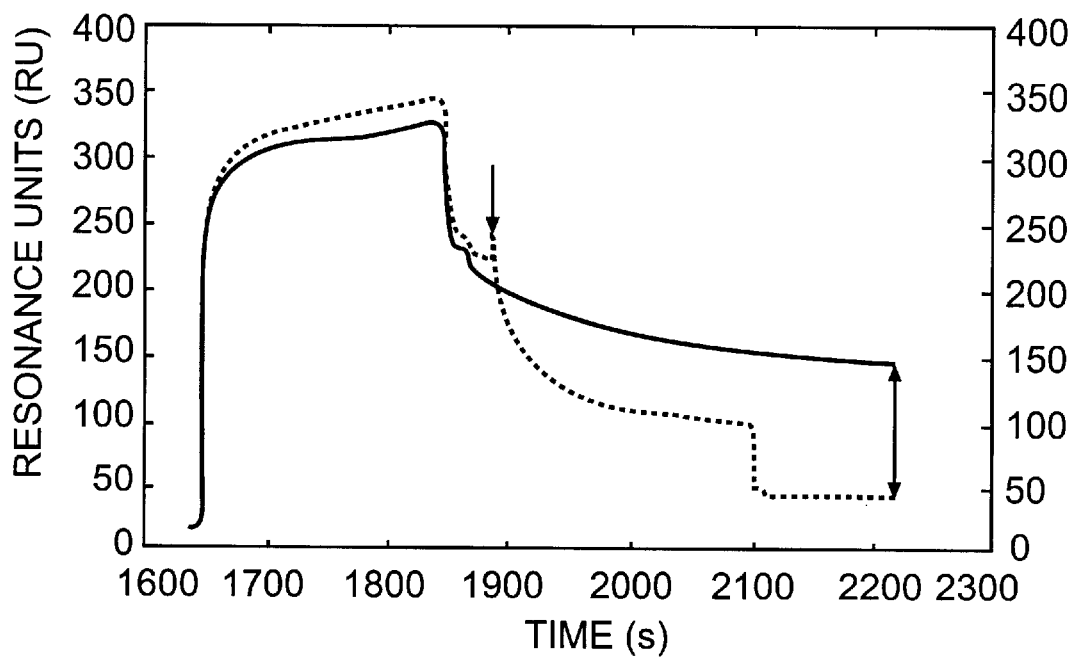
FIG. 9 is a sensorgram (Resonance Units against time, in seconds) showing displacement of CPDTR peptide-conjugate from HMFG1 antibody by KPDQR peptide.

In order to observe whether there had been any displacement of the CPDTR-ovalbumin by the peptide KPDQR, the raw data were analysed in the BIAevaluation package. Essentially, the two regions of data for the binding of CPDTR-ovalbumin conjugate to HMFG1 antibody with and without the following peptide displacement were plotted as separate graphs and overlaid. To keep the data synchronised the graphs were both aligned at the point of injection for the CPDTR-ovalbumin conjugate (see FIG. 9).

The curve with no peptide injected (solid line in FIG. 9) shows the normal dissociation of the CPDTR-ovalbumin conjugate from the HMFG1 antibody. This is essentially the baseline from which the immunospecific displacement is measured.

The curve with peptide added (broken line in FIG. 9) shows the inmunodisplacement. Immediately after the peptide KPDQR injection (denoted by a downward vertical arrow in the Figure) starts there is a sharp rise in the resonance unit signal. This is due to the change from instrument HBS running buffer to the KPDQR peptide buffer and is called "bulk refractive index change". (Bulk refractive index changes occur when samples with buffer composition different from the HBS running buffer of the instrument are injected over the sensor chip. The difference in the ionic strength of the HBS and sample buffers results in a change in the refractive index where the evanescent wave is probing the dextran layer. The refractive index change gives an immediate shift in resonance signal which is observed on the sensorgram.)

This increase in resonance units caused by the bulk refractive index change is rapidly lost because immunodisplacement of the CPDTR-ovalbumin conjugate from the HMFG1 antibody is occurring, and the loss of mass due to this displacement causes a drop in the resonance signal. Eventually the signal curve flattens because the peptide has removed all the CPDTR-ovalbumin conjugate possible and all that remains is multiply bound CPTDR-ovalbumin conjugate which has such high avidity that it cannot be displaced. At the end of the peptide injection there is an immediate drop in the resonance unit signal that is caused by the switch from sample buffer to the HBS instrument running buffer. A comparison of the curves with and without peptide injected, i.e. immunodisplacement versus normal dissociation, shows that there is an additional loss of 100 RU of CPDTR-ovalbumin conjugate from the HMFG1 antibody caused by the KPDQR peptide (indicated by the double-headed vertical arrow in FIG. 9).

From the data presented in these examples one can see how the invention can be used with particular advantage to assay low molecular weight analytes, such as steroids or peptides, without the need to label any of the assay components.

What is claimed is:

1. A method of detecting the presence of an analyte of interest in a sample, the method comprising the steps of:

providing a solid support comprising an analogue of the analyte of interest, said solid support further comprising a binding partner reversibly immobilised thereon by interaction with said analogue, the binding partner having lower binding affinity for the analogue than for the analyte of interest;

specifically displacing the bin din g partner from the solid support in response to the presence of the analyte of interest in the sample, said displacement causing a reduction in the mass of material immobilised on the solid support, thereby generating a detect able change in a mass-dependent property of the solid support; and detecting the presence of said analyte of interest by detecting said change.

2. A method according to claim 1, wherein the reversibly immobilised binding partner is an immunoglobulin or a functional binding fragment thereof.

3. A method according to claim 1, wherein the reversibly immobilised binding partner is a bispecific antibody.

4. A method according to claim 1, wherein the analogue of the analyte of interest is covalently bound to the solid support.

5. A method according to claim 1, wherein the solid support comprises part of a biosensor device.

6. A method according to claim 1, wherein the solid support comprises part of an evanescent wave, acoustic wave or surface plasmon resonance sensor device.

7. A method according to claim 1, wherein the analyte of interest is estradiol, or a metabolite thereof.

8. A method according to claim 1, wherein the analyte of interest is estrone-3-glucuronide or estriol-3-glucuronide.

\* \* \* \* \*